(12) United States Patent
Westbrook et al.

(10) Patent No.: US 8,496,008 B2
(45) Date of Patent: Jul. 30, 2013

(54) ORAL DEVICE FOR RADIOTHERAPY

(75) Inventors: Tony Westbrook, Lafayette, LA (US);
Sheila Wartelle, Carencro, LA (US);
Grover Bass, Sunset, LA (US)

(73) Assignee: Oncologics, Inc., Lafayette, LA (US)

( * ) Notice: Subject to any disclaimer, the term of this patent is extended or adjusted under 35 U.S.C. 154(b) by 290 days.

(21) Appl. No.: 12/961,810

(22) Filed: Dec. 7, 2010

(65) Prior Publication Data

US 2011/0240036 A1    Oct. 6, 2011

Related U.S. Application Data (63) Continuation-in-part of application No. 12/750,903, filed on Mar. 31, 2010.

(51) Int. Cl.
| | |
|---|---|
| *A61G 15/00* | (2006.01) |
| *A61F 5/37* | (2006.01) |
| *A61F 13/00* | (2006.01) |
| *A61F 5/56* | (2006.01) |
| *A61F 11/00* | (2006.01) |
| *A61F 9/00* | (2006.01) |
| *A61C 5/14* | (2006.01) |
| *A61C 3/00* | (2006.01) |

(52) U.S. Cl.
USPC ........... 128/860; 128/845; 128/846; 128/859; 128/861; 128/898; 433/6; 433/7; 433/24; 602/902

(58) Field of Classification Search
USPC .................. 128/846, 848–862, 898; 433/6–7, 433/24; 602/902
See application file for complete search history.

(56) References Cited

U.S. PATENT DOCUMENTS

| | | | | |
|---|---|---|---|---|
| 3,132,647 | A * | 5/1964 | Corniello | 128/848 |
| 4,676,240 | A   | 6/1987 | Gardy | |
| 5,533,523 | A * | 7/1996 | Bass et al. | 128/859 |
| 5,666,973 | A * | 9/1997 | Walter | 128/848 |
| 6,060,083 | A   | 5/2000 | Dorr et al. | |
| 6,244,866 | B1* | 6/2001 | Campbell | 433/140 |
| 6,629,971 | B2  | 10/2003 | McDaniel | |
| 6,655,960 | B2* | 12/2003 | Fischer | 433/140 |
| 6,675,804 | B1* | 1/2004 | Pivovarov | 128/848 |
| 6,676,655 | B2  | 1/2004 | McDaniel | |
| 6,716,029 | B2* | 4/2004 | Fischer et al. | 433/140 |

(Continued)

OTHER PUBLICATIONS

International Search Report dated May 11, 2011 in related PCT Application No. PCT/US11/23567 filed Feb. 3, 2011, 2 pages.

(Continued)

*Primary Examiner* — Patricia Bianco
*Assistant Examiner* — Brandon L Jackson
(74) *Attorney, Agent, or Firm* — Eric L. Sophir; Dentons US LLP (57) ABSTRACT

An oral device for use in radiotherapy of the head and neck includes a base member and a bite member or "mouthpiece," which is selectively positionable relative to the base member. The device provides immobilization of the tongue for accurate reproducible administration of radiation therapy. The device fits within the oral cavity of a patient and is maintained in position by a bite member that fits over the maxillary teeth of the patient. The position of the bite member relative to the base member may be adjustable to accommodate differences in mouth cavities and bite profiles. For example, the base member may include a platform or series of members configured to be removably coupled to the bite member in multiple different positions.

11 Claims, 7 Drawing Sheets

U.S. PATENT DOCUMENTS

| | | | |
|---|---|---|---|
| 6,887,260 | B1 | 5/2005 | McDaniel |
| 6,936,044 | B2 | 8/2005 | McDaniel |
| 6,976,491 | B2 | 12/2005 | D'Agosto |
| 7,004,933 | B2 | 2/2006 | McDaniel |
| 7,107,997 | B1 | 9/2006 | Moses et al. |
| 7,137,393 | B2 * | 11/2006 | Pivovarov .................... 128/848 |
| 7,201,765 | B2 | 4/2007 | McDaniel |
| 7,494,503 | B2 | 2/2009 | McDaniel |
| 7,520,281 | B1 | 4/2009 | Nahabedian |
| 7,607,439 | B2 * | 10/2009 | Li ................................ 128/860 |
| 8,028,705 | B2 * | 10/2011 | Li ................................ 128/860 |
| 8,251,069 | B2 * | 8/2012 | Burdumy et al. ............ 128/861 |
| 8,261,748 | B1 * | 9/2012 | Goldberg ..................... 128/848 |
| 2002/0123746 | A1 | 9/2002 | McDaniel |
| 2002/0144685 | A1 * | 10/2002 | Ivanovich et al. ............ 128/848 |
| 2003/0004499 | A1 | 1/2003 | McDaniel |
| 2003/0129154 | A1 | 7/2003 | McDaniel |
| 2004/0267236 | A1 | 12/2004 | Sun et al. |
| 2005/0149150 | A1 | 7/2005 | McDaniel |
| 2005/0261750 | A1 | 11/2005 | McDaniel |
| 2005/0283211 | A1 | 12/2005 | McDaniel |
| 2006/0129209 | A1 | 6/2006 | McDaniel |
| 2006/0184214 | A1 | 8/2006 | McDaniel |
| 2006/0212025 | A1 | 9/2006 | McDaniel |
| 2006/0217690 | A1 | 9/2006 | Bastin et al. |
| 2006/0265030 | A1 | 11/2006 | McDaniel |
| 2007/0191822 | A1 | 8/2007 | McDaniel |
| 2007/0289600 | A1 * | 12/2007 | Li ................................ 128/860 |
| 2008/0097278 | A1 | 4/2008 | Cole et al. |
| 2009/0131499 | A1 | 5/2009 | Castro et al. |
| 2009/0196903 | A1 | 8/2009 | Kliman |
| 2009/0311347 | A1 | 12/2009 | Oronsky et al. |
| 2010/0132720 | A1 * | 6/2010 | Razmovski .................. 128/848 |
| 2010/0256550 | A1 | 10/2010 | McDaniel |

OTHER PUBLICATIONS

International Search Report dated Apr. 20, 2011 in related PCT Application No. PCT/US11/23572 filed Feb. 3, 2011, 2 pages.

International Search Report dated May 10, 2011 in related PCT Application No. PCT/US11/23575 filed Feb. 3, 2011, 2 pages.

Lacouture et al., Evolving Strategies for the Management of Hand-Foot Skin Reaction Associated with the Multitargeted Kinase Inhibitors Sorafenib and Sunitinib, The Oncologist, 2008, pp. 1001-1011, vol. 13.

Perez-Soler et al., HER1/EFGR Inhibitor-Associated Rash: Future Directions for Management and Investigation Outcomes from the HER1/EGFR Inhibitor Rash Management Forum, The Oncologist, 2005, pp. 345-356, vol. 10.

* cited by examiner

Section A-A    Fig. 14

ORAL DEVICE FOR RADIOTHERAPY

RELATED APPLICATION

This application is a continuation-in-part of U.S. patent application Ser. No. 12/750,903, entitled "Oral Device for Radiotherapy," filed on Mar. 31, 2010, the complete disclosure of which is hereby fully incorporated herein by reference.

TECHNICAL FIELD

The present disclosure relates generally to a device for use during administration of radiation therapy to patients with head and neck cancers, and more specifically, to a mouthpiece to be inserted into the mouth during radiation therapy of the neck or head.

BACKGROUND

Head and neck cancers are a major cause of morbidity and mortality worldwide. Head and neck cancers generally include a group of related cancers originating from the aerodigestive tract. Such cancers may involve the oral cavity, the lips, pharynx, larynx, nasal cavity, and paranasal sinuses. Head and neck cancers also may include cancers of the esophagus.

The incidence of the specific types of head and neck cancer vary greatly throughout the world. For example, although rare in other regions, there is a high incidence of nasopharyngeal carcinoma, a human squamous cell cancer, in Southeast Asia and North Africa. The majority of head and neck cancers are squamous cell carcinomas.

Treatment of head and neck cancer may involve surgery to remove the cancer or radiotherapy and/or chemotherapy to destroy the cancer cells. Radiotherapy or radiation therapy remains the primary treatment for head and neck cancer. Radiotherapy uses high-energy x-rays given as external beam radiotherapy or internal beam radiotherapy to kill cancer cells or to stop them from growing further. Although radiotherapy can affect both cancer cells and normal cells, normal cells are better able to resist or recover from the effects of the radiotherapy.

The area of treatment for head and neck cancer varies. For example, treatment may involve the back of the throat and/or the lymph glands in the neck. The treatment is planned carefully to ensure that the rays are targeted precisely onto the cancerous area, and to do as little harm as possible to the surrounding healthy tissues and minimize side effects such as dry mouth (xerostomia) and inflamed mucous membranes (mucositis). Other side effects from poorly directed radiation include dental decay (caries) and death of bone tissue (osteoradionecrosis).

If the patient can be accurately positioned for repeat sessions of radiotherapy, then side effects may be minimized. In each session, the patient should be disposed in a substantially identical position. This can be difficult to achieve because the patient's lower jaw and tongue tend to change position even when the head is held securely.

A conventional approach to keeping the affected area stable during treatment involves depressing the patient's tongue onto the floor of the patient's mouth using a mouthpiece molded from contoured wax. The mouthpiece helps minimize the movement of the patient's tongue and jaw during the radiation procedure. Wax mouthpieces are disadvantageous at least because they must be molded individually for each patient and may change shape depending on the storage temperature or the temperature inside the patient's mouth.

Therefore, a need exists in the art for an improved means for reducing movement or immobilizing the patient's tongue during radiation treatment.

SUMMARY

The invention is directed to an oral device for use during administration of head and neck radiotherapy. The device includes a base member and a bite member or "mouthpiece" which can be inserted into a patient's mouth for immobilizing the patient's tongue during radiation treatment. The position of the mouthpiece relative to the base member may be adjustable. For example, the base member may include multiple apertures within which a protrusion of the mouthpiece may be selectively positioned. The device may include a hollow base that reduces scattering of radiation as it passes through the device to the affected tissues.

In one aspect, the device includes a base member and an adjustable bite member. The base member and bite member are sized and configured to be positioned at least partially within an oral cavity of a human patient such that the base member depresses the patient's tongue and the bite member accommodates at least certain of the front teeth of the patient's upper jaw during radiation therapy. The base member includes multiple defined attachment points for removably coupling the bite member to the base member. For example, the attachment points can include apertures or protrusions that are each configured to cooperate with a protrusion or aperture, respectively, of the bite member to removably couple the bite member to the base member. The position of the bite member is determined by the attachment point with which it cooperates.

For example, the attachment points may include multiple apertures within a single platform of the base member or apertures that are each included in a separate member of the base member. The platform and separate members may be hollow and accessible through one or more holes in the base member. The attachment points may have different heights relative to the base of the base member. For example, the attachment points may cover three or more different height levels to accommodate various oral cavity sizes and bite profiles.

The base member may include raised structures, such as bumps and/or ridges, which are configured to engage the patient's tongue during the radiation therapy. For example, the raised structures can be arranged in a half circle shape. The oral device may be cast from a non-toxic, biocompatible, and/or biodegradable material that is injection moldable and retains its shape when exposed to radiation.

These and other aspects, objects, features, and embodiments will become apparent to a person of ordinary skill in the art upon consideration of the following detailed description of illustrative embodiments exemplifying the best mode for carrying out the invention as presently perceived.

BRIEF DESCRIPTION OF DRAWINGS

For a more complete understanding of the invention and the advantages thereof, reference is now made to the following description, in conjunction with the accompanying figures briefly described as follows.

DETAILED DESCRIPTION OF THE EXEMPLARY EMBODIMENTS

The invention is directed to an oral device for immobilizing a patient's tongue during administration of radiation therapy for treatment of cancers of the head and neck. The device includes an adjustable mouthpiece to be inserted into an oral cavity of the patient prior to the radiation therapy. The adjustable mouthpiece immobilizes the patient's tongue and opens the patient's jaw to permit irradiation of affected tissue. For example, the mouthpiece may be adjustable to accommodate different mouth cavities and bite profiles. The device optionally may include a substantially hollow base member that minimizes scattering of radiation that would affect healthy surrounding tissues. In certain exemplary embodiments, the device has a relatively small size to permit air to move freely when the device is positioned inside the patient's mouth, thus making it easy for the patient to breathe when the device is positioned inside the patient's mouth.

Figure 1:
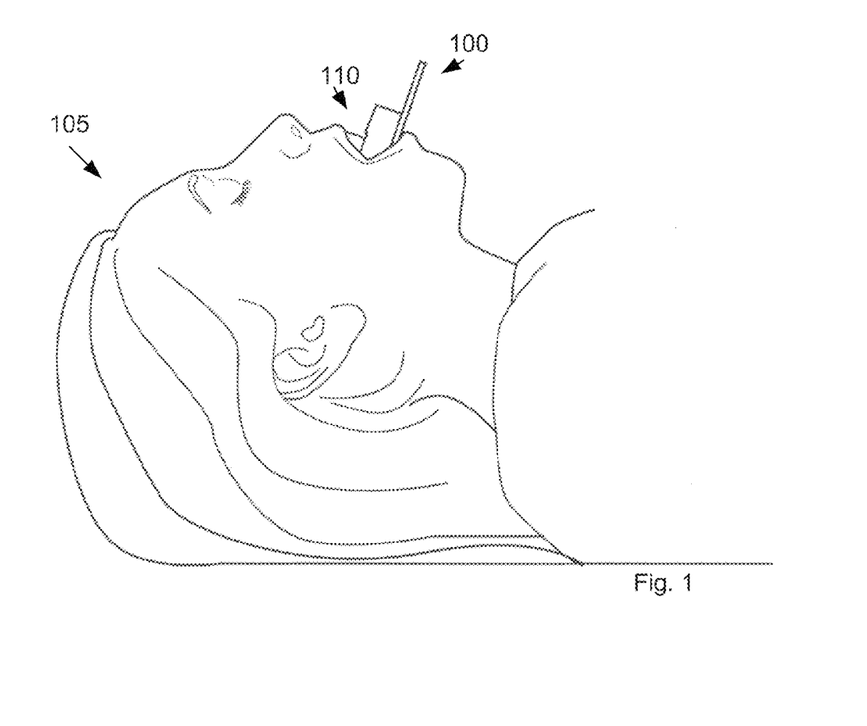
FIG. 1 is a side view of an oral device placed in an oral cavity of a radiotherapy patient, in accordance with certain exemplary embodiments.
Figure 2:
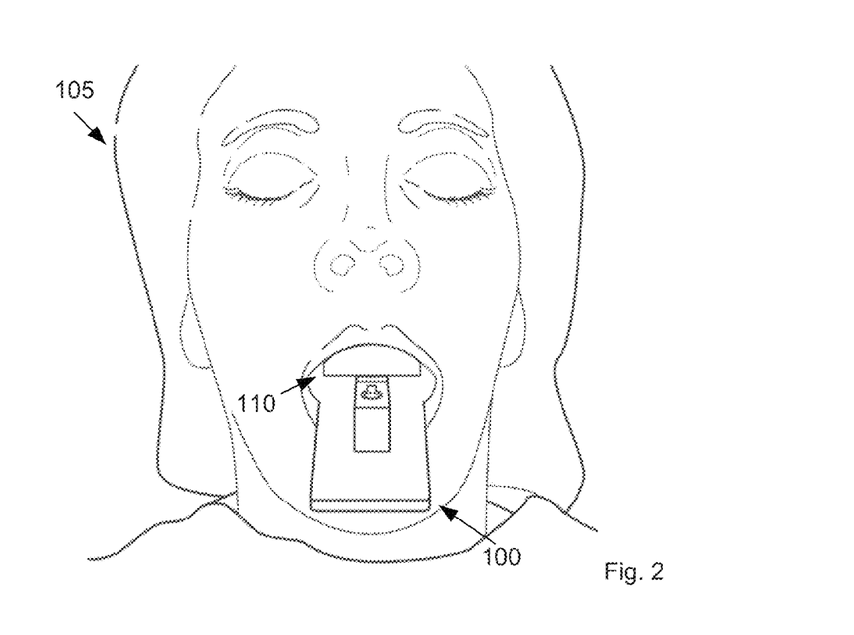
FIG. 2 is a front view of the oral device placed in the oral cavity of the radiotherapy patient, in accordance with certain exemplary embodiments.
Figure 3:
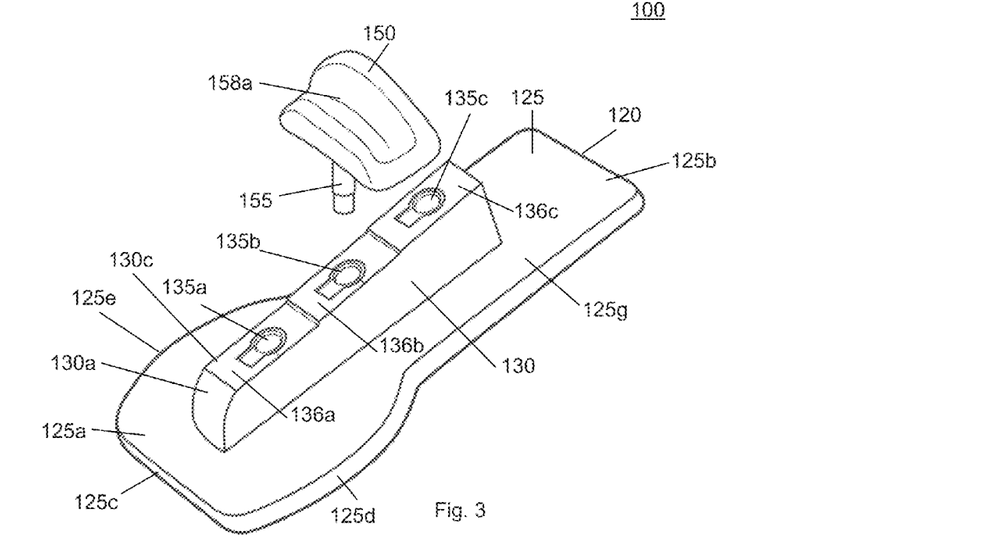
FIG. 3 is an isometric view of the oral device with an adjustable bite member thereof not installed, in accordance with certain exemplary embodiments.

Turning now to the drawings, in which like numerals indicate like elements throughout the figures, exemplary embodiments are described in detail. FIGS. 1-2 illustrate an oral device 100 placed in an oral cavity 110 of a radiotherapy patient 105, in accordance with certain exemplary embodiments. FIGS. 3-8 illustrate the oral device 100, in accordance with certain exemplary embodiments.

With reference to FIGS. 1-8, the oral device 100 includes a base member 120 and a bite member 150. The base member 120 includes a substantially elongated base 125 having a first end 125a and a second end 125b. In certain exemplary embodiments, the base 125 is substantially planar in shape and wider in the lateral dimension at the first end 125a than at the second end 125b.

The first end 125a includes a substantially flat edge 125c disposed between substantially rounded edges 125d and 125e. In certain exemplary embodiments, the substantially rounded edges 125d and 125e have shapes that correspond to interior contours of an average person's cheeks. When the first end 125a is disposed in the patient's 105 oral cavity 110, a bottom surface 125f of the first end 125a can rest on the patient's tongue (not shown), and the rounded edges 125d and 125e can engage interior portions of the patient's cheek. In certain exemplary embodiments, the width of the end 125a can correspond to a desired degree of opening of the user's oral cavity 110. Generally, the larger the width of the end 125a, the larger the opening of the user's oral cavity 110 and vice versa.

A platform 130 extends substantially perpendicularly from a top surface 125g of the base 125. The platform 130 has a first end 130a proximate the first end 125a of the base 125 and a second end 130b proximate the second end 125b of the base 125. In certain exemplary embodiments, the platform 130 has differential heights, increasing from the first end 130a to the second end 130b.

The platform 130 is configured to releasably receive the bite member 150 in at least one position. In the exemplary embodiment depicted in FIGS. 1-8, the platform includes three apertures 135a-135c in a top face 130c of the platform. Each aperture 135a-135c is configured to receive a corresponding protrusion 155 of the bite member 150 to thereby releasably couple the bite member 150 to the platform 130. A person of ordinary skill in the art having the benefit of the present disclosure will recognize that many other means, such as one or more screws, snaps, adhesive tape, Velcro, and the like, may be used to releasably couple the bite member 150 to the platform 130 in certain alternative exemplary embodiments.

In the exemplary embodiment depicted in FIGS. 1-8, the top face 130c of the platform 130 defines three terraced levels 136a-136c that include the apertures 135a-135c, respectively. A person of ordinary skill in the art having the benefit of the present disclosure will recognize that any number of terraced levels 136 may be included in certain alternative exemplary embodiments. For example, in certain alternative exemplary embodiments, one, two, three, four, five, or six terraced levels 136 may be included. Similarly, in certain alternative exemplary embodiments, the top face 130c of the platform may include the apertures 135a-135c without any terraced levels 136. Although depicted in FIGS. 1-8 as inclining from the end 130a to the end 130b, a person of ordinary skill in the art having the benefit of the present disclosure will recognize that the platform 130 may decline or remain flat from the end 130a to the end 130b in certain alternative exemplary embodiments.

Each aperture 135a-135c corresponds to a different position of the bite member 150 in the device 100. The bite member 150 may be removably coupled to the device 100 by inserting the protrusion 155 of the bite member 150 into the aperture 135a-135c corresponding to the desired position of the bite member 150. In certain exemplary embodiments, the desired position may depend on the size of the patient's oral cavity 110 or the patient's bite profile. For example, the bite member 150 may be removably coupled in the aperture 135c when the device 100 is used in connection with a patient 105 having a relatively large sized oral cavity 110; the bite member 150 may be removably coupled in the aperture 135b when the device 100 is used in connection with a patient 105 having an average sized oral cavity 110; and the bite member 150 may be removably coupled in the aperture 135a when the device 100 is used in connection with a patient 105 having a relatively small sized oral cavity 110. The base 125 and platform 130 may be molded together so that the base member 120 is a single continuous unit. Alternatively, the base 125 and platform 130 may be fabricated separately and affixed together to form the base member 120.

The device 100 may be positioned to minimize contact with tissue inside the oral cavity 110. Contact between the device 100 and tissues inside the mouth may cause increased scattering of radiation and minimize the efficacy and targeting of the radiation treatment. To reduce or minimize contact between the bottom surface 125f of the base 125 and the patient's tongue, the bottom surface 125f may include one or more raised structures 126 that function to suppress or immobilize the patient's tongue while minimizing contact between the tongue tissue and the base 125 of the device 100. Although depicted in FIGS. 4 and 6 as substantially round bumps that each extend about two millimeters to about twenty millimeters from the surface 125f, a person of ordinary skill in the art having the benefit of the present disclosure will recognize that the raised structures 126 can have any size or shape in certain alternative exemplary embodiments. For example, each raised structure 126 may be round angular, square, hexagonal, octagonal, or any other shape, and may extend five millimeters to fifteen millimeters, seven millimeters to ten millimeters, or other lengths in certain alternative exemplary embodiments. In certain alternative exemplary embodiments, the raised structures 126 may include a series of ridges that span the underside of the base 125 laterally or longitudinally or at any angle to lateral or longitudinal orientation. As would be recognized by a person of ordinary skill in the art having the benefit of the present disclosure, the raised structures 126 can include a variety of differently-shaped members in certain alternative exemplary embodiments.

In certain exemplary embodiments, the platform 130 is substantially hollow such that apertures 135 connect to a cavity 128 within the platform 130. The bottom surface 125f of the base 125 can include an opening 125h that corresponds to and connects to the cavity 128 in certain exemplary embodiments. In such embodiments, the apertures 135 are visible through the opening 125h when the base 125 is viewed from its bottom surface 125f. In certain alternative exemplary embodiments, the platform 130 may not be hollow.

Figure 4:
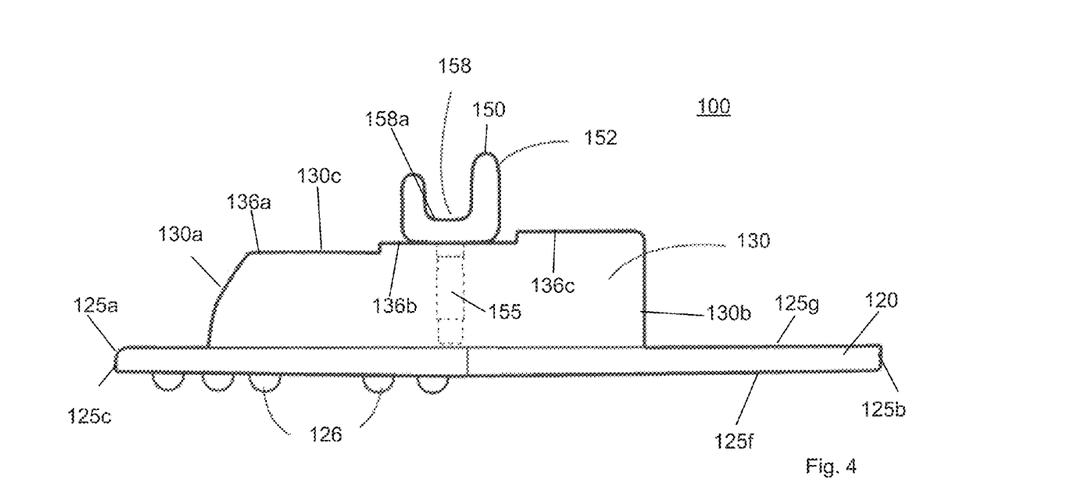
FIG. 4 is a perspective side view of the oral device with the adjustable bite member installed in a central position, in accordance with certain exemplary embodiments.
Figure 5:
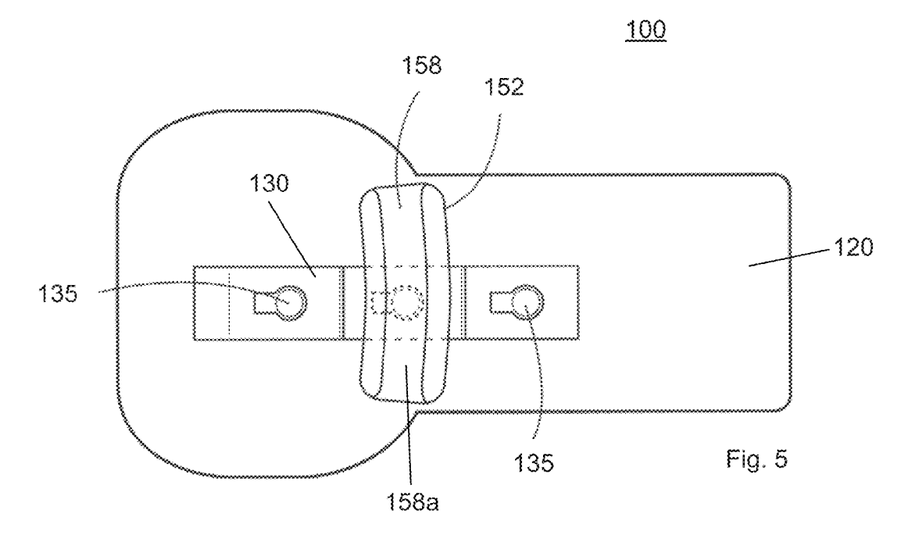
FIG. 5 is a perspective top view of the oral device with the adjustable bite member installed in the central position, in accordance with certain exemplary embodiments.
Figure 6:
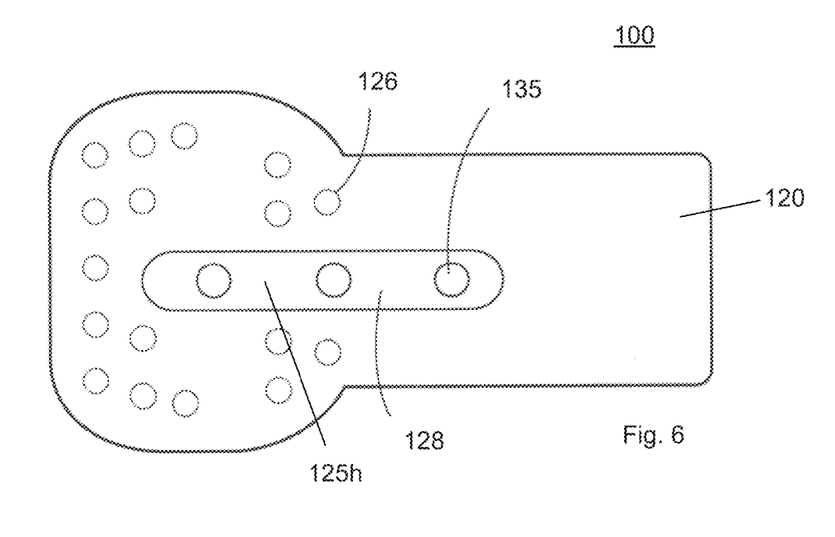
FIG. 6 is a perspective bottom view of the oral device with the adjustable bite member installed in the central position, in accordance with certain exemplary embodiments.
Figure 7:
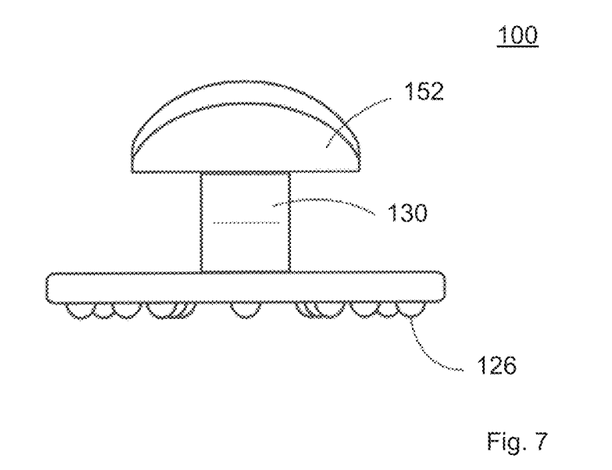
FIG. 7 is a perspective anterior view of the oral device with the adjustable bite member installed in the central position, in accordance with certain exemplary embodiments.
Figure 8:
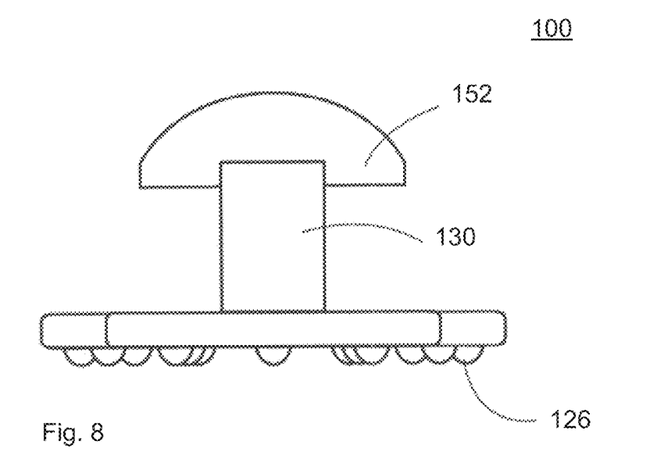
FIG. 8 is a perspective posterior view of the oral device with the adjustable bite member installed in the central position, in accordance with certain exemplary embodiments.
Figure 9:
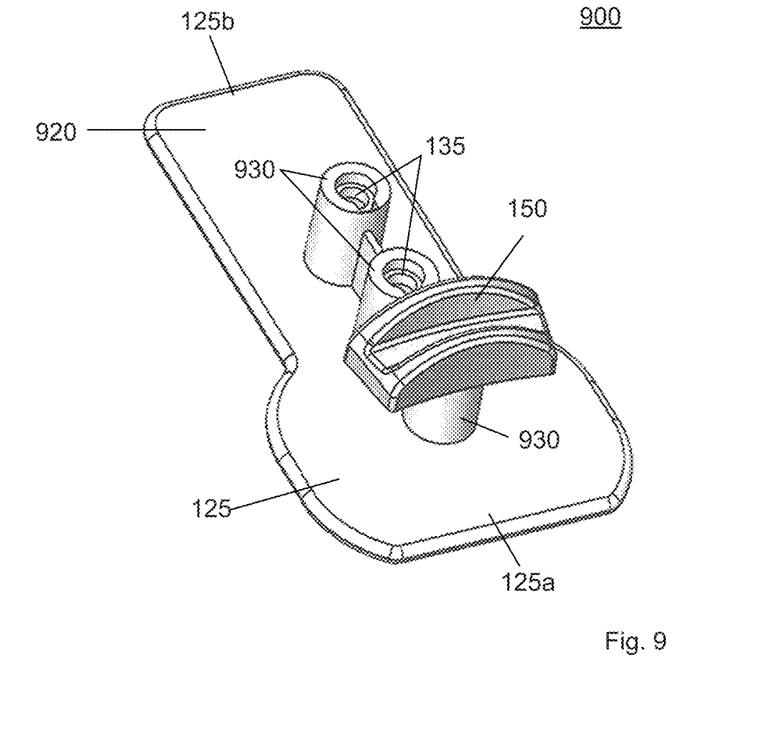
FIG. 9 is an isometric view of an oral device, in accordance with certain alternative exemplary embodiments.
Figure 10:
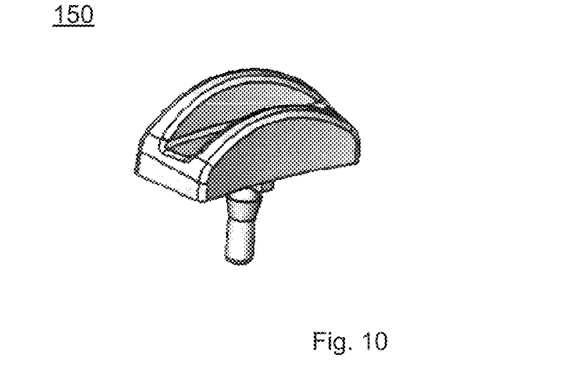
FIG. 10 is an isometric view of a bite member of the oral device of FIG. 9, in accordance with certain alternative exemplary embodiments.
Figure 11:
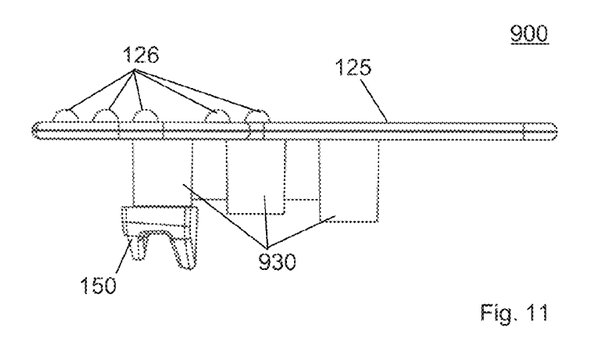
FIG. 11 is a perspective side view of the oral device of FIG. 9, in accordance with certain alternative exemplary embodiments.
Figure 12:
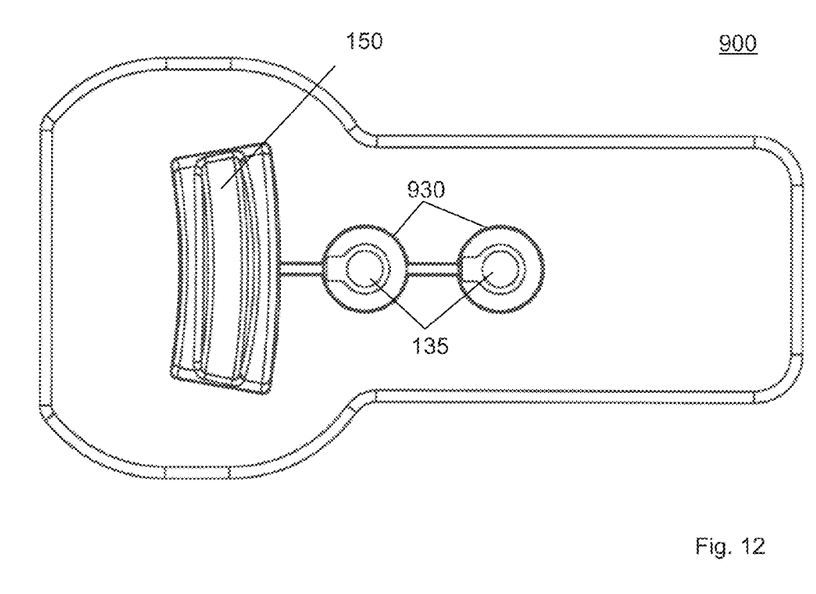
FIG. 12 is a perspective top view of the oral device of FIG. 9, in accordance with certain alternative exemplary embodiments.
Figure 13:
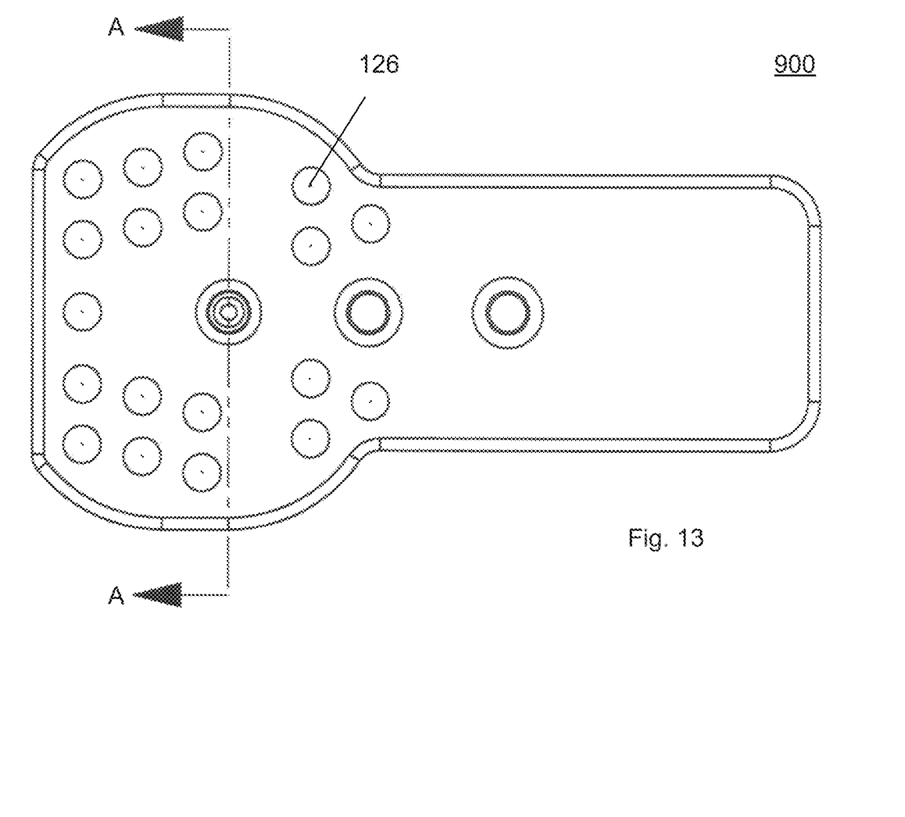
FIG. 13 is a perspective bottom side view of the oral device of FIG. 9, in accordance with certain alternative exemplary embodiments.
Figure 14:
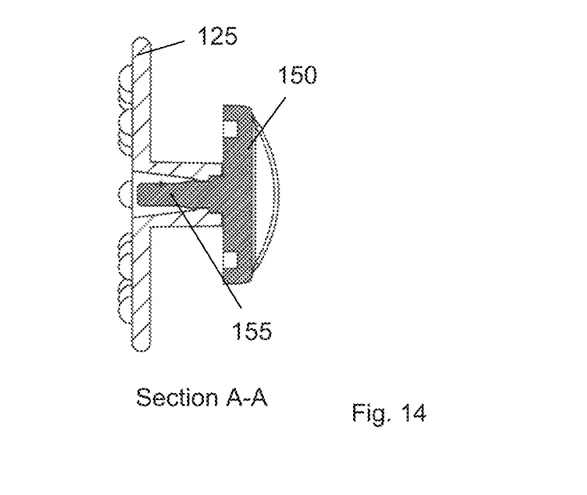
FIG. 14 is a cross-sectional side view of the adjustable bite member of FIG. 9, in accordance with certain alternative exemplary embodiments.

The bite member 150 is separable from the base member 120 and is configured to be removably coupled to the base member 120 by inserting the protrusion 155 of the bite member 150 into a corresponding one of the apertures 135, as illustrated in FIG. 4. The bite member 150 includes a tooth/gum tray 152 having a groove 158, which accommodates the front teeth of the upper jaw of the patient 105. In certain exemplary embodiments, the protrusion 155 includes a key and locking tapered barrel pin, which engages the platform 130 to prevent rotation of the tooth/gum tray 152. In addition or in the alternative, such rotation may be prevented by sizing the protrusion 155 to fit firmly into the apertures 135 of the platform 130. In certain exemplary embodiments, a mirrored receiver cavity is formed in each level 136 of the platform 130 to assist in locking the tooth/gum tray 152 securely to the platform 130.

The groove 158 of the tooth/gum tray 152 is configured to receive a maxillary row of teeth of the patient 105 on a top surface 158a thereof. In certain exemplary embodiments, the tooth/gum tray 152 may have a substantially curved shape so as to generally fit an average maxillary row of teeth from a human, or else may be made of a moldable material that may be pre-molded to substantially conform to the maxillary row of teeth of the patient 105.

In certain exemplary embodiments, the tooth/gum tray 152 is pre-molded before radiation treatment to substantially conform to the patient's maxillary teeth. This permits a customized device 100 that permits reproducible radiotherapy in multiple sessions. In such embodiments, the tooth/gum tray 152 may be made from a radiolucent material, such as Aquaplast RT Thermoplastic, which includes 2-Oxepanone polymer with 1,4-butanediol. The tooth/gum tray 152 may be immersed in water at or around 70° Celsius to soften the material and then inserted into the patient's mouth to obtain an impression of the patient's maxillary teeth. Once the radiolucent material hardens, the tooth/gum tray 152 can be removed from the patient's mouth. This allows for a customized device 100 that is partially reusable. The base member 120 of the device 100 may be sterilized and reused, and the bite member 150 may be discarded after radiation treatment is complete. In certain exemplary embodiments, the bite member 150 and/or the base member 120 are disposable. Effective sterilization methods include but are not limited to autoclave, UV irradiation, and gas sterilization.

FIGS. 9-14 illustrate an oral device 900, in accordance with certain alternative exemplary embodiments. With reference to FIGS. 1-14, the oral device 900 is similar to the oral device 100 except that the base member 920 of the oral device 900 includes members 930 instead of a platform 130. Similar to the platform 130, the members 930 may have the same heights or may have differential heights increasing or decreasing from the first end 125a of the base 125 to the second end 125b of the base 125. Like the platform 130, each member 930 includes an aperture 135 configured to receive the protrusion 155 from the bite member 150 to removably couple the bite member 150 to the base member 920.

The base 125 and the members 930 may be molded together so that the base member 920 is a single continuous unit. Alternatively, the base 125 and the members 930 may be fabricated separately and affixed together after they are created to form the base member 920. Although illustrated in the figures as having substantially cylindrical shapes and apertures 135, a person of ordinary skill in the art having the benefit of the present disclosure will recognize that the members 930 and apertures 135 may have any shape, such as an angular, square, hexagonal, octagonal, or any other shape, in certain alternative exemplary embodiments. Similarly, although illustrated in the figures as having apertures 135 configured to receive a protrusion 155 of the bite member 150, a person of ordinary skill in the art having the benefit of the present disclosure will recognize that, in certain alternative exemplary embodiments, each member 930 (and, in connection with the device 100, the platform 130) may include a protrusion, which may be received within a corresponding aperture in the bite member 150.

Materials

In certain exemplary embodiments, the bite member 150 is made from a soft plastic material to allow for bite compression. Each device 100 and 900 may be made from inert, non-toxic, or biocompatible material(s) that will not react with human tissues when placed into the oral cavity 110 or subjected to radiation of the radiotherapy treatment. In certain exemplary embodiments, at least certain of the materials are FDA-approved for use in human subjects.

In certain exemplary embodiments, the bite member 150 includes a 40-50 Durometer A Scale injection molded material. For example, such a material may include rubber, such as silicone, soft vulcanized rubber, natural nitrile, or the like. Alternatively, the material may include one or more elastomeric materials, such as GR-S, GR-1, neoprene, thiokol, or the like. In certain exemplary embodiments, the material for the base 125 is a flexible, high impact styrene vacuum-formed material (HIPS).

Other materials that may be used to mold an oral device, such as the device 100 or the device 900, may include radiolucent materials, which allow the passage of X-rays or other radiation. For example, such radiolucent materials may include one or more plastics, thermosets, such as phenolics and epoxies, and/or thermoplastics, such as polyolefins, polyesters, nylons, polycarbonates, polyurethanes, and polyketones. The material may also include medical radiolucent composites, such as thermoplastic resins with carbon-fiber reinforcement.

Dimensions

In certain exemplary embodiments, the dimensions of the base 125 and bite member 150 are such that they accommodate being fit into an average human mouth cavity. For example, the base 125 may have a length of about 8-12 cm, about 9-11 cm, or about 10.5 cm. Usually, the end 125b of the base 125 will protrude from the mouth of the patient 105 when the base 125 is positioned therein. Alternatively, the entire base 125 may fit substantially in the mouth of the patient 105 during use. In certain exemplary embodiments, the base 125 measures about 4-7 cm or about 5.0 cm in width at the end 125a and about 2-5 cm or about 3.8 cm at the end 125b. In certain exemplary embodiments, the height of the platform 130 and/or the members 930 may be between 3 and 8 mm or about 5 mm. The width of the platform 130 is not particularly important and will typically range from about 0.8 cm to about 1.8 cm. The height of the base 125 will typically be between about 1.0 cm and 2.5 cm.

A person of ordinary skill in the art will recognize that the dimensions provided herein are merely exemplary in nature and that, in certain alternative exemplary embodiments, alternative dimensions may be utilized without departing from the spirit and scope of the claimed invention.

Use of the Device

Each of the devices 100 and 900 described herein can be used during radiotherapy of the head and neck to immobilize the patient's tongue and open the patient's jaw during radiation treatment. The device 100/900 is positioned inside the patient's mouth so that the patient's upper row of teeth rests in the groove 158 of the tooth/gum tray 152, substantially as illustrated in FIGS. 1 and 2. The bite member 150 is removably coupled to the platform 130 or a member 930 via positioning the protrusion 155 of the bite member 150 in a selected aperture 135. The bite member 150 permits a secure fit of the device 100/900 in the patient's mouth. The position of the bite member 150 may be selected based on the size of the patient's mouth and/or the patient's bite profile. The device 100/900 is positioned to depress the patient's tongue to minimize or reduce tongue movement or immobilize the tongue. Placement of the device 100/900 in the patient's mouth also opens the patient's jaw and provides reproducible positioning of the jaw and tongue for specific exposure to radiation during radiotherapy. The optional hollow platform 130 can minimize scattering of radiation to healthy surrounding tissues.

Although specific embodiments of the invention have been described above in detail, the description is merely for purposes of illustration. It should be appreciated, therefore, that many aspects of the invention were described above by way of example only and are not intended as required or essential elements of the invention unless explicitly stated otherwise. Various modifications of, and equivalent steps corresponding to, the disclosed aspects of the exemplary embodiments, in addition to those described above, can be made by a person of ordinary skill in the art, having the benefit of this disclosure, without departing from the spirit and scope of the invention defined in the following claims, the scope of which is to be accorded the broadest interpretation so as to encompass such modifications and equivalent structures.

What is claimed is:

1. An oral device for use in radiation therapy, comprising:
a base member; and
a bite member, each of the base member and the bite member sized and configured to be positioned at least partially within an oral cavity of a human patient such that the base member depresses the patient's tongue and the bite member accommodates at least certain of the front teeth of the patient's upper jaw during the radiation therapy,
wherein the base member comprises a plurality of defined attachment points for removably coupling the bite member to the base member, the bite member selectively positionable between the attachment points to adjust a location of the bite member relative to the base member, and
wherein a face of the base member opposite the bite member comprises a plurality of raised structures configured to engage the patient's tongue during the radiation therapy.

2. The oral device of claim 1, wherein the base member comprises:
a substantially elongated base; and
a platform extending from a face of the base, the defined attachment points comprising at least two apertures in the platform, each of the apertures configured to removably receive a protrusion of the bite member.

3. The oral device of claim 2, wherein the apertures are located at different heights relative to the substantially elongated base.

4. The oral device of claim 1, wherein the base member comprises a substantially hollow cavity that reduces scattering of radiation from the radiation therapy.

5. An oral device for use in radiation therapy, comprising:
a base member, wherein the base member comprises:
a substantially elongated base; and
a plurality of members extending from a face of the substantially elongated base, the defined attachment points comprising an aperture in each of the members, each aperture configured to removably receive a protrusion of the bite member, wherein each of the members comprises a substantially cylindrical member, wherein each substantially cylindrical member extends substantially perpendicularly from the face of the substantially elongated base; and
a bite member, each of the base member and the bite member sized and configured to be positioned at least partially within an oral cavity of a human patient such that the base member depresses the patient's tongue and the bite member accommodates at least certain of the front teeth of the patient's upper jaw during the radiation therapy,
wherein the base member comprises a plurality of defined attachment points for removably coupling the bite member to the base member, the bite member selectively positionable between the attachment points to adjust a location of the bite member relative to the base member.

6. The oral device of claim 5, wherein the plurality of members vary in height relative to the substantially elongated base.

7. The oral device of claim 5, wherein a face of the base member opposite the bite member comprises a plurality of raised structures configured to engage the patient's tongue during the radiation therapy.

8. The oral device of claim 5, wherein the oral device is composed of a radiolucent material.

9. An oral device for use in radiation therapy, comprising:
a base member; and
a bite member, each of the base member and the bite member sized and configured to be positioned at least partially within an oral cavity of a human patient such that the base member depresses the patient's tongue and the bite member accommodates at least certain of the front teeth of the patient's upper jaw during the radiation therapy,
wherein the base member comprises
a substantially elongated base,
a plurality of members extending from a first face of the substantially elongated base, each of the members comprising an aperture configured to removably receive a protrusion of the bite member to thereby removably couple the bite member to the base member, the bite member selectively positionable within the apertures to adjust a location of the bite member relative to the base member, and
a plurality of raised structures rising from a second face of the base member opposite the bite member and configured to engage the patient's tongue during the radiation therapy.

10. An oral device for use in radiation therapy, comprising:
a base member; and
a bite member, each of the base member and the bite member sized and configured to be positioned at least partially within an oral cavity of a human patient such that the base member depresses the patient's tongue and the bite member accommodates at least certain of the front teeth of the patient's upper jaw during the radiation therapy,
wherein the base member comprises
a substantially elongated base, and
a plurality of members extending from a first face of the substantially elongated base, each of the members comprising an aperture configured to removably receive a protrusion of the bite member to thereby removably couple the bite member to the base member, the bite member selectively positionable within the apertures to adjust a location of the bite member relative to the base member, wherein each of the members comprises a substantially cylindrical member, wherein each substantially cylindrical member extends substantially perpendicularly from the face of the substantially elongated base.

11. The oral device of claim 10, wherein the oral device is composed of a radiolucent material.

* * * * *

UNITED STATES PATENT AND TRADEMARK OFFICE
CERTIFICATE OF CORRECTION

Page 1 of 3

PATENT NO. : 8,496,008 B2
APPLICATION NO. : 12/961810
DATED : July 30, 2013
INVENTOR(S) : Tony Westbrook et al.

It is certified that error appears in the above-identified patent and that said Letters Patent is hereby corrected as shown below:

On the Title Page

Delete title page and substitute the attached title page therefor.

In the Claims

Column 8, line 31:

Please insert --2. The oral device of claim 1, wherein the base member comprises a substantially hollow cavity that reduces scattering of radiation from the radiation therapy--.

Column 8, line 31:

Please correct "2. The oral device of claim 1..." to --3. The oral device of claim 2...--.

Column 8, line 38:

Please correct "3. The oral device of claim 2..." to --4. The oral device of claim 3...--.

Column 8, line 41:

Please correct "4. The oral device of claim 1..." to --5. The oral device of claim 1...--.

Column 8, line 44:

Please correct "5. An oral device for use in radiation therapy comprising:" to --6. An oral device for use in radiation therapy comprising:--.

Signed and Sealed this
Twenty-fourth Day of June, 2014

Michelle K. Lee
*Deputy Director of the United States Patent and Trademark Office*

CERTIFICATE OF CORRECTION (continued)
U.S. Pat. No. 8,496,008 B2

Column 9, line 1:

Please correct "6. The oral device of claim 5..." to --7. The oral device of claim 6...--.

Column 9, line 4:

Please correct "7. The oral device of claim 5,..." to --8. The oral device of claim 6...--.

Column 9, line 8:

Please correct "8. The oral device of claim 5,..." to --9. The oral device of claim 6...--.

Column 9, line 11:

Please correct "9. An oral device for use in radiation therapy, comprising:" to --10. An oral device for use in radiation therapy, comprising:--.

Column 10, line 5:

Please correct "10. An oral device for use in radiation therapy, comprising:" to --11. An oral device for use in radiation therapy, comprising--.

Column 10, line 27:

Please correct "11. The oral device of claim 10..." to --12. The oral device of claim 11...--.

(12) United States Patent
Westbrook et al.

(10) Patent No.: US 8,496,008 B2
(45) Date of Patent: Jul. 30, 2013

(54) ORAL DEVICE FOR RADIOTHERAPY (75) Inventors: Tony Westbrook, Lafayette, LA (US); Sheila Wartelle, Carencro, LA (US); Grover Bass, Sunset, LA (US)

(73) Assignee: Oncologics, Inc., Lafayette, LA (US)

( * ) Notice: Subject to any disclaimer, the term of this patent is extended or adjusted under 35 U.S.C. 154(b) by 290 days.

(21) Appl. No.: 12/961,810

(22) Filed: Dec. 7, 2010

(65) Prior Publication Data
US 2011/0240036 A1 Oct. 6, 2011

Related U.S. Application Data

(63) Continuation-in-part of application No. 12/750,903, filed on Mar. 31, 2010.

(51) Int. Cl.
| | |
|---|---|
| A61G 15/00 | (2006.01) |
| A61F 5/37 | (2006.01) |
| A61F 13/00 | (2006.01) |
| A61F 5/56 | (2006.01) |
| A61F 11/00 | (2006.01) |
| A61F 9/00 | (2006.01) |
| A61C 5/14 | (2006.01) |
| A61C 3/00 | (2006.01) |

(52) U.S. Cl.
USPC ......... 128/860; 128/845; 128/846; 128/859; 128/861; 128/898; 433/6; 433/7; 433/24; 602/902

(58) Field of Classification Search
USPC ............... 128/846, 848–862, 898; 433/6–7, 433/24; 602/902
See application file for complete search history.

(56) References Cited

U.S. PATENT DOCUMENTS

| | | | | |
|---|---|---|---|---|
| 3,132,647 | A * | 5/1964 | Corniello | 128/848 |
| 4,676,240 | A | 6/1987 | Gardy | |
| 5,533,523 | A * | 7/1996 | Bass et al. | 128/859 |
| 5,666,973 | A * | 9/1997 | Walter | 128/848 |
| 6,060,083 | A | 5/2000 | Dorr et al. | |
| 6,244,866 | B1 * | 6/2001 | Campbell | 433/140 |
| 6,629,971 | B2 | 10/2003 | McDaniel | |
| 6,655,960 | B2 * | 12/2003 | Fischer | 433/140 |
| 6,675,804 | B1 * | 1/2004 | Pivovarov | 128/848 |
| 6,676,655 | B2 | 1/2004 | McDaniel | |
| 6,716,029 | B2 * | 4/2004 | Fischer et al. | 433/140 |

(Continued)

OTHER PUBLICATIONS

International Search Report dated May 11, 2011 in related PCT Application No. PCT/US11/23567 filed Feb. 3, 2011, 2 pages.

(Continued)

*Primary Examiner* — Patricia Bianco
*Assistant Examiner* — Brandon L Jackson
(74) *Attorney, Agent, or Firm* — Eric L. Sophir; Dentons US LLP (57) ABSTRACT

An oral device for use in radiotherapy of the head and neck includes a base member and a bite member or "mouthpiece," which is selectively positionable relative to the base member. The device provides immobilization of the tongue for accurate reproducible administration of radiation therapy. The device fits within the oral cavity of a patient and is maintained in position by a bite member that fits over the maxillary teeth of the patient. The position of the bite member relative to the base member may be adjustable to accommodate differences in mouth cavities and bite profiles. For example, the base member may include a platform or series of members configured to be removably coupled to the bite member in multiple different positions.

12 Claims, 7 Drawing Sheets